United States Patent
Hansen et al.

(10) Patent No.: US 11,209,382 B2
(45) Date of Patent: Dec. 28, 2021

(54) CALIBRATION CONCEPT FOR AMPEROMETRIC CREATININE SENSOR CORRECTING FOR ENDOGENOUS MODULATORS

(71) Applicant: Radiometer Medical ApS, Brønshøj (DK)

(72) Inventors: Thomas Steen Hansen, Herlev (DK); Thomas Kjaer, Smorum (DK); Thomas Pedersen Nygaard, Herlev (DK)

(73) Assignee: Radiometer Medical APS, Bronshoj (DK)

( * ) Notice: Subject to any disclaimer, the term of this patent is extended or adjusted under 35 U.S.C. 154(b) by 353 days.

(21) Appl. No.: 15/536,910

(22) PCT Filed: Dec. 14, 2015

(86) PCT No.: PCT/EP2015/079524
§ 371 (c)(1),
(2) Date: Jun. 16, 2017

(87) PCT Pub. No.: WO2016/096683
PCT Pub. Date: Jun. 23, 2016

(65) Prior Publication Data
US 2017/0363568 A1 Dec. 21, 2017

(30) Foreign Application Priority Data
Dec. 18, 2014 (DK) .......................... PA 2014 00736

(51) Int. Cl.
*G01N 27/327* (2006.01)
*G01N 33/70* (2006.01)
*C12Q 1/00* (2006.01)

(52) U.S. Cl.
CPC ......... *G01N 27/3274* (2013.01); *C12Q 1/002* (2013.01); *C12Q 1/005* (2013.01); (Continued)

(58) Field of Classification Search
CPC ...... C12Q 1/002; C12Q 1/005; C12Y 105/03; C12Y 105/03001; C12Y 305/0201; (Continued)

(56) References Cited

U.S. PATENT DOCUMENTS

| 5,527,706 A | 6/1996 | Kroneis et al. |
| 2004/0072277 A1 | 4/2004 | Schaffar et al. |

(Continued)

FOREIGN PATENT DOCUMENTS

| CN | 101175999 A | 5/2008 |
| EP | 0 291 321 A2 | 11/1988 |

(Continued)

OTHER PUBLICATIONS

ABL700 Series Reference Manual, Manufacturer: Radiometer, Publication: 201003, Edition: Q.

(Continued)

*Primary Examiner* — Joshua L Allen
(74) *Attorney, Agent, or Firm* — Finnegan, Henderson, Farabow, Garrett & Dunner, LLP

(57) ABSTRACT

A method of calibrating a device for measuring the concentration of creatinine in a sample including one or more enzyme modulators, the method comprising: determining sensitivities of the device for each of two or more calibration solutions, wherein each calibration solution has a different amount of enzyme modulator; determining a degree of modulation for each of the two or more calibration solutions; determining a degree of modulation for a sample to be measured; and calculating the sensitivity of the device for the sample, wherein said calculating comprises modifying (Continued)

the sensitivity of one of the two or more calibration solutions by a function comprising the determined degrees of modulation.

10 Claims, 4 Drawing Sheets

(52) U.S. Cl.
CPC . *C12Y 105/03001* (2013.01); *C12Y 305/0201* (2013.01); *G01N 33/70* (2013.01); *G01N 2333/90683* (2013.01); *G01N 2333/986* (2013.01)

(58) Field of Classification Search
CPC ..... G01N 27/3274; G01N 2333/90683; G01N 2333/986; G01N 33/70
See application file for complete search history.

(56) References Cited

U.S. PATENT DOCUMENTS

| | | | | |
|---|---|---|---|---|
| 2006/0275857 | A1* | 12/2006 | Kjaer | C12Q 1/002 435/23 |
| 2006/0275859 | A1* | 12/2006 | Kjaer | C12Q 1/002 435/25 |
| 2006/0275860 | A1* | 12/2006 | Kjaer | C12Q 1/34 435/27 |
| 2008/0000780 | A1* | 1/2008 | Tonks | G01N 27/3274 205/792 |
| 2009/0247856 | A1* | 10/2009 | Boock | C12Q 1/006 600/347 |
| 2010/0159606 | A1 | 6/2010 | Nakaminami et al. | |
| 2010/0258451 | A1* | 10/2010 | Adlassnig | G01N 27/3273 205/777.5 |

FOREIGN PATENT DOCUMENTS

| | | |
|---|---|---|
| EP | 1 715 347 A1 | 10/2006 |
| JP | 61-270650 | 11/1986 |
| JP | 2004-506224 | 2/2004 |
| JP | 2005-241537 | 9/2005 |
| JP | 2007-512519 | 5/2007 |
| JP | 2008-511554 | 4/2008 |
| JP | 2009-271075 | 11/2009 |
| WO | WO 03/019165 A2 | 3/2003 |
| WO | WO 2008/034587 A1 | 3/2008 |
| WO | WO 2014/134537 A1 | 9/2014 |

OTHER PUBLICATIONS

International Search Report for International Application No. PCT/EP2015/079524, dated Mar. 24, 2016.
Written Opinion of the International Searching Authority for International Application No. PCT/EP20154/079524.

* cited by examiner

| | | | |
|---|---|---|---|
| Hydrogen carbonate (Bicarbonate) | Acetate | Guanodinoacetate | N-Carbamoylsarcosine |
| Inhibitor | Inhibitor | Weak inhibition Substrate | Strong inhibition |
| $I_{50} = 9$ mM | $I_{50} = 9.6$ mM | $I_{50} = 36$ mM | $I_{50} = 0.45$ mM |

| Succinamic acid | Succinate | Hydantoic acid |
|---|---|---|
| Inhibitor | Inhibitor | Inhibitor |
| $I_{50} = 1.5$ mM | $I_{50} = 2.4$ mM | $I_{50} = 2.4$ mM |

Fig 3

```
Determine sensitivities of the device for each of two or more      410
calibration solutions (sens_Cal2 and sens_Cal3)
                            ↓
Determine a degree of enzyme modulation for each of the            420
two or more calibration solutions (mod_Cal1 and mod_Cal3)
                            ↓
Determine a degree of enzyme modulation for a sample to be         430
measured (mod_sam)
                            ↓
Calculate the sensitivity of the device for the sample (sens_sam)  440
                            ↓
Determine the concentration of creatine and/or creatinine          450
using the calculated sensitivity of the device for the sample
```

Fig 4

CALIBRATION CONCEPT FOR AMPEROMETRIC CREATININE SENSOR CORRECTING FOR ENDOGENOUS MODULATORS

This application is a national stage filing under 35 U.S.C. § 371 of International Application No. PCT/EP2015/079524, filed on Dec. 14, 2015, which claims priority of Danish Patent Application No. PA 2014 00736, filed Dec. 18, 2014. The contents of these applications are each incorporated herein by reference.

FIELD OF THE INVENTION

The invention relates to methods for calibrating creatinine and creatine measuring devices, and calibration solutions for use in those methods.

BACKGROUND

Techniques for measuring the concentration of creatinine (Crn) and creatine (Cr) have uses in medicine, for example in monitoring renal disease. The concentration of Cr (cCr) and the concentration of Crn (cCrn) in an aqueous solution can be determined by amperometric measurement. Two sensors can be used in the measurement of cCrn: the Crea A sensor, which detects Cr; and the Crea B sensor, which detects both Cr and Crn. The cCrn is based on the difference between the Crea A and Crea B sensor measurements.

Sensors typically use enzymes to convert creatinine and creatine into measurable products, such as hydrogen peroxide which can be detected in an amperometric system. In order to determine cCrn and cCr in unknown samples with sufficient accuracy, the Crea A and Crea B sensors must be calibrated in order to determine their actual sensitivities.

However, the presence of enzyme modulators in a sample can modulate (i.e. increase or decrease) the activity of the enzymes in the sensor. Therefore, a sensor calibrated with a calibration solution that has a different amount or type of enzyme modulator than the sample being measured may yield inaccurate results.

Enzyme modulators can occur naturally in samples being measured, and may occur in unpredictable amounts. For example, bicarbonates are enzyme inhibitors and are endogenous to blood, and different people will have different concentrations of bicarbonates in their blood. Therefore, it is not possible to prepare a single calibration solution having a bicarbonate concentration matching all possible samples of human blood plasma. More generally, it is acknowledged that preparing a calibration solution having the same degree of enzyme modulation as in a target sample can be difficult to achieve.

Existing solutions include adding acetate in a concentration showing an enzyme modulation level similar to that being present in blood. This solution is only accurate for blood samples carrying an average level of modulators, and even in this case sensors may respond differently to different modulators because of differences in diffusional transport characteristics.

There is, therefore, an unmet need for an efficient method of calibrating creatine and/or creatinine sensors to take into account different levels of enzyme modulation in measured samples.

SUMMARY OF THE INVENTION

In a first aspect of the present invention, the applicant makes available a method of calibrating a device for measuring the concentration of creatinine in a sample including one or more enzyme modulators, the method comprising: determining sensitivities of the device for each of two or more calibration solutions, wherein each calibration solution has a different amount of enzyme modulator; determining a degree of modulation for each of the two or more calibration solutions; determining a degree of modulation for a sample to be measured; and calculating the sensitivity of the device for the sample, wherein said calculating comprises modifying the sensitivity of one of the two or more calibration solutions by a function comprising the determined degrees of modulation.

By using two calibration solutions with different amounts of enzyme modulators, it is possible to calculate how a measuring device is affected by enzyme modulators to predict the effect of any level of enzyme modulation in a measured sample.

In some example embodiments the one or more enzyme modulators include an acid or an alkali or a salt thereof.

In some example embodiments, the one or more enzyme modulators include one or more of: bicarbonate, acetate, formate, $Ca^{2+}$, and $Zn^{2+}$.

In some example embodiments, pH functions as an enzyme modulator.

In some example embodiments, said determining the sensitivities of the device for two or more calibration solutions comprises calculating a ratio between an output of the device in the calibration solution and a concentration of creatinine and/or creatine in the calibration solution.

In some example embodiments, said determining a degree of modulation for each of the calibration solutions comprises estimating enzyme modulation based on the amounts of enzyme modulators in the calibration solutions.

In some example embodiments, said determining a degree of modulation for each of the calibration solutions comprises receiving a value of said degree of modulation.

In some example embodiments, said function further comprises a ratio between enzyme activity and permeability of the device.

In some example embodiments, the ratio between enzyme activity and permeability of the device is a dimensionless constant specific to the device.

In some example embodiments, one of the two or more calibration solutions has an amount of enzyme modulator of the same order of magnitude as the sample.

In some example embodiments, one of the two or more calibration solutions has no enzyme modulator, or a low level of enzyme modulator.

In some example embodiments, one of the two or more calibration solutions has a high level of enzyme modulation, which is at least substantially higher than the low or zero level enzyme modulator.

In some example embodiments, the device is a creatine and/or creatinine sensor.

According to another aspect of the present invention, a computer readable medium is provided comprising instructions which when executed by one or more processors of an electronic device, cause the electronic device to operate in accordance with any of the aforementioned methods.

According to another aspect of the present invention, an electronic device is provided comprising: one or more processors; and memory comprising instructions which when executed by one or more of the processors cause the electronic device to operate in accordance with any of the aforementioned methods.

According to another aspect of the present invention, a package is provided comprising two or more calibration solutions, wherein each calibration solution has a different amount of enzyme modulator; and instructions for use with any of the aforementioned methods or aforementioned electronic devices.

BRIEF DESCRIPTIONS OF DRAWINGS

Examples of the present proposed apparatus will now be described in detail with reference to the accompanying drawings, in which:

FIG. 3 is a table showing examples of enzyme modulators; and

FIG. 4 is a flowchart outlining the steps of the proposed method.

DETAILED DISCLOSURE

Figure 1:
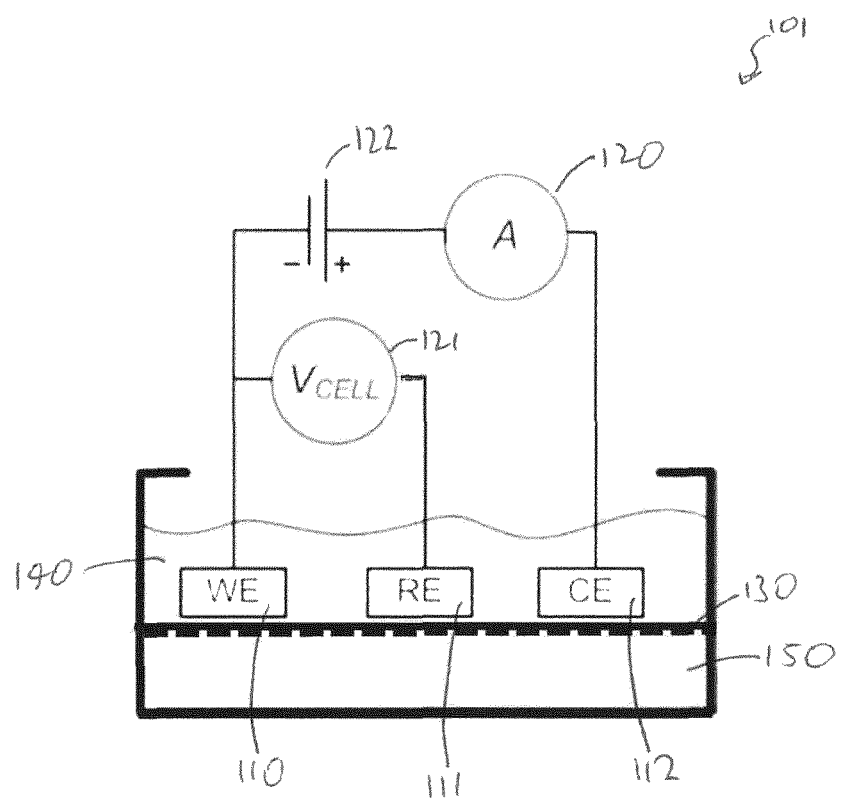
FIG. 1 is a schematic diagram of an example of an amperometric measuring system.

Reference will now be made to FIG. 1 which is a schematic diagram of a three electrode amperometric measuring system 101. An amperometric measuring system may have at least two electrodes: a working electrode (WE) 110 and a combined counter and reference electrode (CE/RE). For the three-electrode amperometric measuring system 101, the functions of the CE/RE electrode are split into two separate electrodes: the reference electrode (RE) 111 and the counter electrode (CE) 112. The example amperometric measuring system 101 also includes an ammeter 120, a voltmeter 121 and a voltage source 122 and the electrolyte solution 140.

The WE 110 is a positively charged electrode where an oxidation reaction occurs. The RE 111 is typically made of Ag/AgCl and is able to maintain a stable potential, especially if no current runs through it, thus the need for a CE 112 for passing the current from the WE 110 back to the electrolyte solution 140. The electrolyte solution 140 and the sample 150 provide ionic contact between the three electrodes. The membrane 130 selectively converts the analyte to a substance that selectively is allowed to pass through from the sample 150. The voltage source 122 applies the necessary potential for maintaining the desired reduction or oxidation reaction, this is controlled by the voltmeter 121. The ammeter 120 measures the resulting current flowing through the electrical circuit, which is a measure of the free flowing electrons due to the chemical reactions between the sample 150 and the electrolyte solution 140.

The amperometric measuring system shown in FIG. 1 is an illustrative example, and several other implementations are envisioned. For example, the amperometric measuring system could be a two electrode system as mentioned above.

The magnitude of an electrical current flowing through the electrode chain is proportional to the concentration of the substance being oxidized (or reduced) at the WE 110. Ideally, when knowing the proportionality constant relating the electrical current to a concentration, the concentration in any given sample can be obtained by measuring the electrical current generated by that particular sample.

To illustrate the measuring process in an amperometric measuring system, we assume that: The sample 150 contains species B, which in the membrane 130 is selectively converted to species A, which can be oxidized at the WE 110 (WE) to $A^+$; and the electrolyte 140 contains species X which is reduced at the CE 112 (cathode) to $X^-$. We assume also that the membrane 130 allows only species A to pass from the sample into the electrolyte solution 140.

As an appropriate potential is applied across the electrodes, A is oxidized at the WE 110 according to the following reaction:

$$A \rightarrow A^- + e^-$$

The oxidation of A produces a flow of electrons. To complete the electrical circuit a reduction reaction where electrons are consumed is necessary. Therefore species X is reduced at the CE 112 according to the following reaction:

$$X + e \rightarrow X^-$$

The magnitude of the current flowing through the circuit is proportional to the concentration of the analyte being oxidized. The analyser can therefore automatically calculate the concentration of the analyte in the sample given species X is in excess.

The term sensor refers to a complete amperometric measuring system, as shown in FIG. 1 excluding the sample 150.

Crn is not stable in aqueous solutions, e.g. blood, where it is reversibly converted into Cr (see Scheme 1). To measure cCr, a Creatine sensor is used (Crea A).

To measure cCrn, a two-sensor system can be used where one sensor (Crea A) detects Cr only, and the other sensor (Crea B) detects both Cr and Crn. By means of a difference measurement it is possible to obtain the cCrn value.

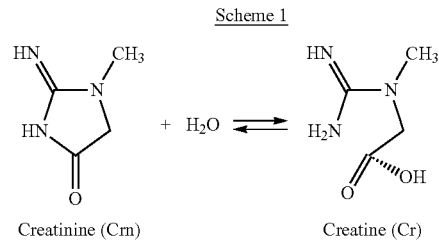

Scheme 1

The sensor is protected by a multilayer membrane 130 consisting of at least three functional layers, namely the outer membrane layer permeable to Crn and Cr; the middle enzyme layer, and the inner membrane layer permeable to $H_2O_2$.

In another embodiment, cCrn is determined directly with a sensor that essentially only has a sensitivity towards Crn. This may be done by applying an outer membrane that is impermeable towards Cr but permeable to Crn, which is feasible since Cr is an anion and Crn is neutral.

Figure 2:
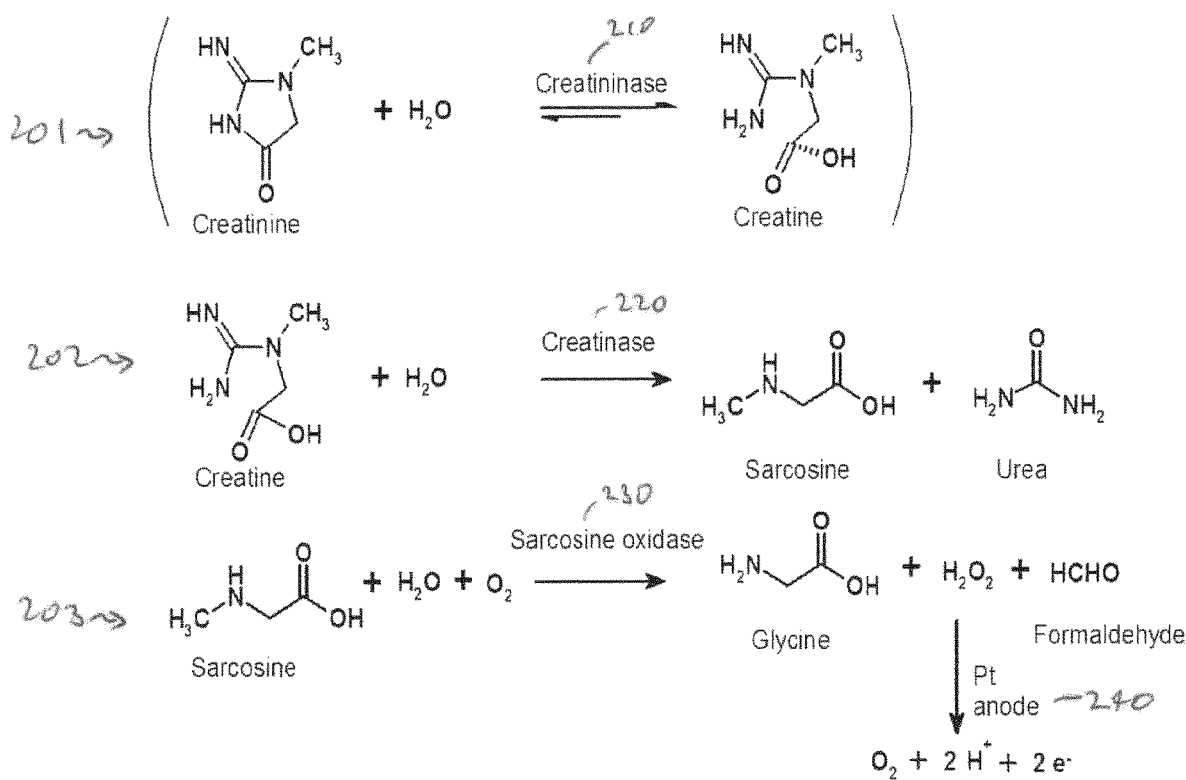
FIG. 2 is a series of diagrams illustrating the enzyme cascade for conversion of creatinine to hydrogen peroxide.

FIG. 2 illustrates an example enzyme cascade for the conversion of creatine and creatinine into hydrogen peroxide. In this example, enzymes creatinase (creatine amidinohydrolase) 220, sarcosine oxidase 230 and creatininase (creatinine amidohydrolase) 210 are used in the enzyme cascade. These enzymes are immobilized between the inner and outer membrane layers, while Crn and Cr molecules can diffuse across the outer membrane layer.

The Crea A sensor detects creatine by converting creatine to hydrogen peroxide in accordance with reactions 202 and 203. To achieve this conversion, the Crea A sensor uses creatine amidinohydrolase 220 and sarcosine oxidase 230. In the Crea A sensor, the enzymatic cascade changes Cr as follows:

Creatine+H$_2$O→sarcosine+urea(creatine amidinohydrolase)

Sarcosine+H$_2$O+O$_2$→glycine+formaldehyde+H$_2$O$_2$ (sarcosine oxidase)

The Crea B sensor contains all three enzymes creatinine amidohydrolase 210, creatine amidinohydrolase 220 and sarcosine oxidase 230, and so detects both Crn and Cr. In the enzymatic cascade Crn/Cr involves reactions 201, 202 and 203:

Creatinine+H$_2$O⇌creatine(creatinine amidohydrolase)

Creatine+H$_2$O→sarcosine+urea(creatine amidinohydrolase)

Sarcosine+H$_2$O+O$_2$→glycine+formaldehyde+H$_2$O$_2$ (sarcosine oxidase)

For both the Crea A and the Crea B sensors the enzyme reactions lead to identical end-products, one of which is H$_2$O$_2$ that can diffuse across the inner membrane layer to the WE 110 (preferably platinum). By applying a sufficiently high electrical potential to the electrode chains of the Crea A and Crea B sensors, H$_2$O$_2$ can be oxidized at the Pt anode 240:

H$_2$O$_2$→2H$^+$+O$_2$+2e$^-$

To complete the electrical circuit, electrons are consumed in reduction reactions at the CE 112 thereby maintaining a charge balance between the WE 110 and the CE 112.

The oxidation of H$_2$O$_2$ produces an electrical current (dE) proportional to the amount of H$_2$O$_2$, which in turn is directly related to the amount of Cr for the Crea A and the amount of Cr and Crn for the Crea B sensors according to the sensor response models:

$$dE_A = Sens_{A,Cr} \cdot [Cr]_A \quad \text{Equation 1}$$

$$dE_B = Sens_{B,Crn} \cdot [Crn]_B + Sens_{B,Cr} \cdot [Cr]_B \quad \text{Equation 2}$$

Where $dE_A$ and $dE_B$ are the electrical currents produced at the Crea A and Crea B sensors respectively; $Sens_{A,Cr}$ and $Sens_{B,Cr}$ are the sensitivity constants relating current (dE) to Cr concentration in the Crea A and Crea B sensors respectively and $Sens_{B,Crn}$ is the sensitivity constant relating current (dE) to Crn concentration in the Crea B sensor.

The proportionality constants, Sens, relating currents to concentrations are typically referred to as sensitivities. The constants are determined by calibrating the sensors. The current (signal) of each sensor is measured by ammeters 120 in the analyser. If sensor sensitivities S are known, the unknown Crn concentration in a given sample is readily determined from the equations above.

The reactions illustrated in FIG. 2 can be modulated by enzyme modulators. Such enzyme modulators may be endogenous to the sample, such as bicarbonates, and these enzyme modulators may inhibit the action of any of the enzymes used. The term enzyme modulator includes substances that reduce the performance of enzymes (inhibitors) or increase the performance of the enzymes.

FIG. 3 shows a number of examples of endogenous modulators that may be present in the sample. The table shows the example modulators along with a measure of their effectiveness in modulating enzymes, namely the I$_{50}$ value (half maximal inhibitory concentration) in mM. Enzyme modulators are not limited to specific molecules, and may include other factors such as the pH or temperature of a solution or sample. It is known that factors like the pH of a solution can affect the performance of the enzyme, so factors such as pH may be referred to herein as enzyme modulators.

In an example embodiment, calibration solutions are set up to determine the effect of pH and bicarbonate concentrations on the sensor readings for a Cr sensor. In this example embodiment, the concentration of Cr is measured using the Crea A sensor, but it is envisioned that the solution may be adapted to measure the concentration of Crn using Crea A and Crea B sensors.

In this example embodiment, the sensor is calibrated using two calibration solutions denoted Cal2 and Cal3. The following scheme shows the content of the two solutions and a given sample:

TABLE 1

|  | Cal2 | Cal3 | Sample |
| --- | --- | --- | --- |
| cCr [μM] | 943 | 487 | TBD |
| pH | 6.8 | 7.1 | 7.4 |
| [HCO$_3$] [mM] | 0 | 24 | 53.2 |
| pCO$_2$ [mmHmg] | 0 | 80 | 82.9 |
| dESample (readout) [pA] | 31179 | 14235 | 2640 |
| Sensitivity ([Cr]/dESample) [pA/μM] | 33.1 | 29.2 | TBD |

Table 1 shows how the calibration solutions Cal2 and Cal3 have known concentrations of Cr and HCO$_3^-$, known pH levels, and known CO$_2$ partial pressures. Calibrators Cal2 and Cal3 may also contain buffers, salts, preservatives and detergents, but in this example embodiment those will be ignored.

The sample, which may be a blood sample to be measured, and may have its pH, HCO$_3^-$ concentration and CO$_2$ partial pressure measured by appropriate sensors. A raw reading (dESample) of the sample can be measured using the amperometric measuring device, but the sensitivity needs to be determined before a Cr concentration can be determined for the sample.

As the Cr concentrations of Cal2 and Cal3 are known, the sensitivities of the sensor for the calibration solutions can be calculated by measuring the ratio between the measured device output (dE) and the known concentrations:

$$sens_{Cal2} = \frac{dECal2}{[Cr]_{Cal2}} = \frac{31179 \text{ pA}}{943 \text{ μM}} \quad \text{Equation 3}$$

$$sens_{Cal3} = \frac{dECal3}{[Cr]_{Cal3}} = \frac{14235 \text{ pA}}{487 \text{ μM}} \quad \text{Equation 4}$$

The readout for each calibration solution (dECal) is recorded and transformed into a sensitivity ratio:

$$\frac{sens_{Cal3,2enz}}{sens_{Cal2,2enz}} = \frac{\frac{dECal3}{[Cr]_{Cal3}}}{\frac{dECal2}{[Cr]_{Cal2}}} = \frac{\frac{14235}{487 \text{ μM}}}{\frac{31179 \text{ pA}}{943 \text{ μM}}} = 0.883 \quad \text{Equation 5}$$

The ratio 0.883 illustrates that the sensor gives 12.3% less current per μM creatine in a solution like Cal3 than in the bicarbonate free solution Cal2. The degree of modulation (mod) is calculated for both calibrations solutions using the known pH (pH_Cal2 and pH_Cal3), and [HCO$_3^-$]([HCO$_3^-$]$_{cal2}$ and [HCO$_3^-$]$_{cal3}$):

$$\text{mod}_{Cal2} = \frac{Ka}{10^{-pH\_Cal2} + Ka} \frac{1}{(1 + [HCO_3^-]_{Cal2}/K_i)} = 0.137 \quad \text{Equation 6}$$

$$\text{mod}_{Cal3} = \frac{Ka}{10^{-pH\_Cal3} + Ka} \frac{1}{(1 + [HCO_3^-]_{Cal3}/K_i)} = 0.025 \quad \text{Equation 7}$$

Equation 6 and 7 may be derived by skilled person by multiplying the equation for protolyzation of a single base and the expression of simple competitive inhibition.

The degree of modulation ($\text{mod}_{cal2}$ and $\text{mod}_{cal3}$) provides an estimate for how much the enzyme is modulated in the given pH and bicarbonate. $K_a$ is the acid ionization constant for the calibration solution, while $K_i$ is the inhibition constant. For the given example 86.3% (1-0.137) and 97.5% (1-0.025) of the original enzyme activity is expected to be removed by inhibition in Cal2 and Cal3, respectively.

From the known modulation values and the sensitivity ratios, one can calculate a sensor specific constant phi ($\varphi$). Phi is a dimensionless constant that is an expression of the ratio between enzyme activity and the permeability of the sensor. In the example embodiment provided, the value for phi is given by:

$$\varphi = \frac{1}{\text{mod}_{Cal3}\left(\frac{sens_{Cal2}}{sens_{Cal3}} - 1\right)} + \frac{1}{\text{mod}_{Cal2}\left(\frac{sens_{Cal3}}{sens_{Cal2}} - 1\right)} = 238.3 \quad \text{Equation 8}$$

Once a sample is aspirated, the modulation of the sensor with the pH and bicarbonate from this specific sample can be calculated:

$$\text{mod}([pH]_{enz}, [HCO_3^-]_{Enz}) = \frac{Ka}{10^{-pH_{rinse}} + \left(10^{-pH_{sample}} - 10^{-pH_{rinse}}\right)} \\ \frac{C_3\left(\left|pCO_{2_{Sam}} - pCO_{2_{Rinse}}\right|\right) + Ka}{\frac{1}{(1 + [HCO_3^-]_{enz}/K_i)}} \\ = 0.015 \quad \text{Equation 9}$$

Equation 9 is a rewriting of equation 6 and 7, where an extra term is added that accounts for the effect of $pCO_2$ on the pH in the sensor.

Here the $pH_{rinse}$ value is the pH is the rinse solution the sensor is exposed to between samples, $pCO_{2_{rinse}}$ is the partial pressure of $CO_2$ in a rinse solution the sensor is exposed to between samples, and $C_3$ is a constant fixed for all sensors and correlates to the permeability of $CO_2$.

The sensitivity in the given sample is calculated by adjusting the sensitivity of one of the calibration solutions by a factor. The factor is a function of the degree of modulation of the sample and the calibration solution, and may also include the value phi. In this example, the sensitivity for Cal3 ($sens_{Cal3}$) is adjusted because the degree of modulation in Cal3 is closer to the degree of modulation of the sample than in Cal2. In this example, the factor is given by:

$$\frac{1 - \frac{1}{\varphi \text{mod}_{Sam} + 1}}{1 - \frac{1}{\varphi \text{mod}_{Cal3} + 1}} \quad \text{Equation 10}$$

In this example the adjusting factor is roughly 0.89, and therefore the sensitivity for the sample is equal to the sensitivity for Cal3 multiplied by this factor:

$$sens_{Sam,Cr} = sens_{Cal3} \frac{1 - \frac{1}{\varphi \text{mod}_{Sam} + 1}}{1 - \frac{1}{\varphi \text{mod}_{Cal3} + 1}} = 26.2 \text{ pA}/\mu\text{M} \quad \text{Equation 11}$$

Using the readout on the given sample (e.g. dESamp=2640 pA) gives the corrected creatine content:

$$[Cr]_{Sam} = \frac{dESamp}{sens_{Sam,Cr}} = \frac{2640 \text{ pA}}{26.2 \text{ pA}/\mu\text{M}} = 100.8 \text{ }\mu\text{M} \quad \text{Equation 12}$$

If the concentration had been calculated using the sensitivity of Cal3 instead of the sensitivity taking into account enzyme modulators, the concentration found would be about 10% lower:

$$[Cr]_{Sam} = \frac{dESamp}{sens_{Cal3}} = \frac{2640 \text{ pA}}{28.8 \text{ pA}/\mu\text{M}} = 91.7 \text{ }\mu\text{M} \quad \text{Equation 13}$$

Furthermore, if the concentration was calculated using the sensitivity of Cal2, which does not have any bicarbonate enzyme modulators, the concentration of Cr would be 79.6 μM, which differs greatly from the concentration calculated using the proposed method. This illustrates that the proposed solution provides improved results over existing methods that do not take into account enzyme modulators when calibrating sensors using calibration solutions.

FIG. 4 outlines the steps for carrying out an example embodiment of the proposed method. The proposed method is not limited to the ordering of the steps shown in FIG. 4, nor is the method envisioned to be solely limited to this example embodiment provided.

At step 410, sensitivities of the device for each of the two or more calibration solutions are determined. Said determining of sensitivities may involve calculating the ratio between an amperometer output (current) and the known concentration of creatine or creatinine of the calibration solution. In some embodiments, the concentrations of creatine or creatinine of the calibration solutions need to be determined or adjusted from an initial concentration, while in other embodiments the concentrations are provided as data accompanying the calibration solutions.

Two calibration solutions or different amounts of enzyme modulators may be provided, effectively providing two data points for determining the relationship between enzyme modulators and sensitivity. Providing more than two calibration solutions of different amounts of enzyme modulators may lead to more accurate results. One calibration solution may be chosen to have very low or no enzyme modulators, while another calibration solution may be chosen to have enzyme modulators around the same order of magnitude as the expected amount of enzyme modulators in samples. In this way, the second calibration solution a sensitivity close to the expected samples, while the first calibration solution provides sensitivities sufficiently distant from the second calibration solution to provide a good measure of the relationship between enzyme modulation and sensitivity.

At step 420, the degree of enzyme modulation is determined for each of the two or more calibration solutions. This degree of enzyme modulation is a measure of how much enzyme activity is modulated in a given solution. For example, where a bicarbonate [$HCO_3^-$] concentration and higher-than-optimum alkalinity (pH) is present, this may inhibit the enzyme activity by a certain percentage given by the degree of modulation. In such an example, the known values for [$HCO_3^-$], pH, $K_a$ and $K_i$ may be used to determine this. Alternatively, the determining may simply involve having the degree of enzyme modulation being entered as an input. In this example, the value may be known from a database or reference source, and may be input as a known, dimensionless variable for use in the method.

At step 430, the degree of enzyme modulation is determined for the sample to be measured. This determining may be similar to the determining of the degrees of enzyme modulation in step 420. The determination of the degree of enzyme modulation for the sample may also take into account the fact that rinsing may occur between samples, which may affect the contribution of pH, for example. While step 420 may be performed once for each set of calibration solutions, step 430 may be repeated for each sample being measured.

At step 440, the sensitivity of the measuring device is calculated for the sample. This step may involve determining a factor by which to adjust one of the sensitivities already determined for one of the calibration solutions. The sensitivity for the calibration solution with a degree of enzyme modulation closest to the degree of enzyme modulation of the sample may be the sensitivity that is adjusted.

The factor that adjusts the sensitivity of the calibration solution may be a function of the degree of enzyme modulation for that calibration solution and the sample. The factor may further be a function of a sensor specific constant that is an expression of the ratio between enzyme activity and the permeability of the device. This sensor specific constant may be calculated after step 420 and before step 430 and may be re-used in the calculation of sensitivities for any further samples measured using the proposed method.

At step 450, the sensitivity for the sample may be used to determine an accurate concentration of creatine or creatinine of the sample by measuring the raw output of the amperometer and dividing it by the calculated sensitivity.

It is to be understood that the present disclosure includes permutations of combinations of the optional features set out in the embodiments described above. In particular, it is to be understood that the features set out in the appended dependent claims are disclosed in combination with any other relevant independent claims that may be provided, and that this disclosure is not limited to only the combination of the features of those dependent claims with the independent claim from which they originally depend.

The invention claimed is:

1. A method for calibrating device sensitivity of an enzymatic amperometric device for measuring a concentration of creatinine and/or creatine in a sample comprising one or more enzyme modulators, wherein said device sensitivity is the sensitivity of the device to the sample, the method comprising:

providing an enzyme amperometric device;

providing two or more calibration solutions wherein the two or more calibration solutions comprise creatinine and/or creatine;

measuring device output for the two or more calibration solutions;

determining calibration sensitivities of the device to each of the two or more calibration solutions by calculating a ratio between the output of the device in each of the two or more calibration solutions and a known concentration of creatinine and/or creatine in each of the two or more calibration solutions, wherein each calibration solution has a different amount of enzyme modulator;

determining a degree of modulation for each of the two or more calibration solutions by estimating enzyme modulation based on the amounts of enzyme modulators in each of the two or more calibration solutions;

determining a degree of modulation for the sample to be measured based on the amounts of enzyme modulators in the sample;

calculating the device sensitivity wherein said calculating comprises adjusting the calibration sensitivity of the device to one of the two or more calibration solutions by a factor, and calibrating the device based on the calculated device sensitivity;

wherein the factor is a function of the determined degree of modulation of the sample and of one of the two or more calibration solutions, and wherein the calibration sensitivity that is adjusted is the calibration sensitivity of the one or more calibration solutions that has a degree of enzyme modulation closest to the degree of enzyme modulation of the sample.

2. The method of claim 1, wherein the one or more enzyme modulators include an acid or an alkali or a salt thereof.

3. The method of claim 1, wherein the one or more enzyme modulators comprise one or more of bicarbonate, acetate, formate, $Ca^{2+}$, $Zn^{2+}$, and pH.

4. The method of claim 1, wherein said determining a degree of modulation for each of the calibration solutions comprises receiving a value of said degree of modulation.

5. The method of claim 1, wherein the device is a creatine and/or creatinine sensor, and wherein the device further comprises a membrane covering the device and facing the sample and said function further comprises a ratio between enzyme activity and permeability of the sensor.

6. The method of claim 1, wherein one of the two or more calibration solutions has a level of enzyme modulation and another calibration solution has a higher level of enzyme modulation.

7. The method of claim 1, wherein one of the two or more calibration solutions has a level of enzyme modulation.

8. The method of claim 1, wherein the device is a creatine and/or creatinine sensor.

9. A computer readable medium comprising instructions which when executed by one or more processors of an electronic device, cause the electronic device to operate in accordance with the method as claimed in clam 1.

10. An electronic device comprising:
one or more processors; and
memory comprising instructions which when executed by one or more of the one or more processors cause the electronic device to operate in accordance with the method claimed in claim 1.

* * * * *